United States Patent [19]

Gibbs

[11] Patent Number: 4,661,493
[45] Date of Patent: Apr. 28, 1987

[54] TIOCONAZOLE AND RELATED COMPOUNDS FOR CONTROL OF HERPES SIMPLEX VIRUS

[75] Inventor: David L. Gibbs, New York, N.Y.

[73] Assignee: Pfizer Inc., New York, N.Y.

[21] Appl. No.: 837,658

[22] Filed: Mar. 6, 1986

Related U.S. Application Data

[63] Continuation of Ser. No. 717,423, Mar. 29, 1985, abandoned.

[51] Int. Cl.$^4$ .................. A61K 31/50; A61K 31/415; A61K 31/445; A61K 31/495
[52] U.S. Cl. .................................. 514/252; 514/396; 514/397; 514/329
[58] Field of Search ................ 514/252, 397, 396, 329

[56] References Cited

U.S. PATENT DOCUMENTS

| | | | |
|---|---|---|---|
| 4,247,552 | 1/1981 | Hallesy et al. | 424/250 |
| 4,277,475 | 7/1981 | Vickery | 424/250 |
| 4,315,001 | 2/1982 | Blough | 424/180 |

*Primary Examiner*—Jerome D. Goldberg
*Attorney, Agent, or Firm*—Charles J. Knuth; Albert E. Frost; Peter C. Richardson

[57] ABSTRACT

Topical vaginal forms of tioconazole and related antimicrobic compounds, especially miconazole, econazole, clotrimazole, butaconazole and ketoconazole, are useful for the control (chemotherapeutic and chemoprophylactic) of Herpes virus infections.

7 Claims, No Drawings

TIOCONAZOLE AND RELATED COMPOUNDS FOR CONTROL OF HERPES SIMPLEX VIRUS

This is a continuation of application Ser. No. 717,423, filed on Mar. 29, 1985, now abandoned.

BACKGROUND OF THE INVENTION

1. Field of the Invention

This invention relates to the use of tioconazole and related imidazole antifungal agents for the control (chemoprophylactic and chemotherapeutic) of Herpes simplex virus (HSV), especially of genital herpes.

2. Description of the Invention

Tioconazole, 1-[2-{(2-chloro-3-thienyl)methoxy)-2-(2,4-dichlorophenyl}ethyl]-1H-imidazole, and related 1-aryl-2-(1-imidazolyl)alkyl ethers and thioethers are described in U.S. Pat. No. 4,062,966, issued Dec. 13, 1977, as antifungal agents for animals, including human, use. Said compounds may be administered in a variety of forms such as suppositories or pessaries or they may be applied topically in the form of, for example, creams, ointments or dusting powders.

U.S. Pat. No. 4,247,552, issued Jan. 27, 1981, discloses the spermatostatic and spermatocidal activity of tioconazole and related compounds, including econazole, miconazole, ketoconazole and clotrimazole, said compounds being administered intravaginally as creams, spray foams, sponges and the like to subjects clinically asymptomatic of vaginal microbial infection.

Control of sexually transmitted diseases, including herpes infections, continues to be an intensively investigated field in view of the major health problems posed by said infections.

U.S. Pat. No. 4,315,001, issued Feb. 9, 1982, discloses the treatment of *Herpes simplex* virus type 1 and type 2 infections in humans by administration of 2-deoxy-D-glucose either alone or in combination with an antifungal agent such as miconazole or miconazole nitrate.

A variety of aryloxyalkylpyrazoles which exhibit in vitro activity against HSV types 1 and 2 and in vivo activity against mouse genital HSV2 are described in U.S. Pat. Nos. 4,171,365; 4,209,526; 4,232,161; 4,234,725 and 4,261,928.

It is interesting and surprising, to note that although tioconazole and the above-enumerated antifungal imidazoles have been known for several years to have spermatostatic and spermatocidal activity, and have been used for the treatment of vaginitis, there have been no reports of their use or other topical antimicrobics to control herpetic infections (HSV1 and 2). If indeed any such use occurred it was unintended and unappreciated; it was an unrecognized accident. Further, none of the reported studies or uses of said compounds were conducted with the intent of controlling herpetic infections. Their purpose was treatment of existing fungal and STD infections; cure rather than prevention. There is, in fact, no known prior use of said compounds which can be considered to have consistently achieved control of herpetic infections.

Few drugs are known for the treatment of *Herpes simplex* type 1 infections and even fewer for the treatment of *Herpes simplex* type 2 infections. Both infections, but especially HSV2, genital Herpes, are sexually transmitted and pose a major health problem. There is, therefore, a pressing need for agents for the prophylactic and/or therapeutic treatment of persons subject to exposure to said infection and/or those suffering from said infection. The ability of a given drug to act both prophylactically and therapeutically is especially desirable.

SUMMARY OF THE INVENTION

It has now been found that tioconazole, miconazole, econazole, clotrimazole, ketoconazole, and butaconazole are effective agents (drugs) for the control of HSV1 and 2 (herpetic infections) on inanimate objects as well as in animals and humans subject to exposure thereto and/or infected thereby. They are highly valuable for the control of herpetic infections and especially for control of HSV2 in humans. The term "control" as used herein includes the chemoprophylaxis (or prevention) and chemotherapy (or treatment) of herpetic infections. When used for such purposes said agents are applied topically. They present a convenient, safe and efficacious procedure for the prevention and treatment of Herpes infections. Their use as regards Herpes is all the more surprising in view of the viral nature of said infection.

Also valuable for the same purpose and in the same way are pharmaceutically acceptable acid addition salts of tioconazole and the other compounds enumerated above. By said salts is meant those salts formed by said compounds with acids which form non-toxic acid addition salts therewith. Representative of such salts are the hydrochloride, hydrobromide, acetate, sulfate, maleate, gluconate and p-toluenesulfonate.

The chemical names of the drugs described herein are presented below:

| Drug | Chemical Name |
| --- | --- |
| tioconazole | 1-[2-[(2-chloro-3-thienyl)methoxy]-2-(2,4-dichlorophenyl)ethyl]-1H—imidazole. |
| miconazole | 1-[2-(2,4-dichlorophenyl)-2-[2,4-dichlorophenyl)methoxy]ethyl]-1H—imidazole. |
| econazole | 1-[2-[(4-chlorophenyl)methoxy[-2-(2,4-dichlorophenyl)ethyl]-1H—imidazole. |
| clotrimazole | 1-[(2-chlorophenyl)diphenylmethyl]-1H—imidazole. |
| ketoconazole | 1-acetyl-4[4-[[2-(2,4-dichlorophenyl)-2-(1H—imidazol-1-ylmethyl)-1,3-dioxolan-4-yl]-methoxy]phenyl]piperazine. |
| butaconazole | 1-[4-(4-chlorophenyl)-2-[(2,6-dichlorophenyl)thio]butyl]-1H—imidazole. |

DETAILED DESCRIPTION OF THE INVENTION

For the control of herpetic infections on inanimate objects or surfaces; i.e., basically as disinfectants, the herein described drugs and/or their pharmaceutically acceptable salts are generally applied in the form of dilute solutions or suspensions in organic or aqueous-organic solvents such as ethanol, acetone or dimethylsulfoxide and mistures thereof with each other or water. They are applied to the locus on which control of herpetic infections is desired in an anti-herpetic controlling amount by immersing, spraying or swabbing said locus. Concentrations of drug ranging from about 1% to about 10% by weight, or an equivalent weight of a pharmaceutically acceptable salt thereof, are used. In general, concentrations at the lower end of this range; i.e., from about 1% to about 5%, are effective in disinfecting inanimate surfaces.

For the control of herpetic infections in animals and humans the herein-described drugs and/or their pharmaceutically acceptable acid addition salts are administered topically to the locus to be protected or treated. For the control of genital herpes; i.e., HSV2 infections, said drugs and/or their pharmaceutically acceptable acid addition salts are administered intravaginally preferably in admixture with a pharmaceutical carrier. Said carrier is, of course, chosen with regard to the intended route and method of administration. In the present invention administration is accomplished topically; i.e., to a definite place or locus, in this instance, for example, the vagina, in the form of a cream, ointment, foam, jelly, tablet, ovule or other suitable composition which lends itself to a topical vaginal dosage form. Creams and ointments are preferred forms.

Suitable creams comprise an aqueous emulsion of polyethylene glycols or liquid petrolatum and from 1% to 10% by weight of drug or an equivalent weight of a pharmaceutically acceptable acid addition salt thereof. Typical ointments comprise a white wax or white soft petrolatum base together with such stabilizers and preservatives as may be required and from 1% to 10% by weight of tioconazole.

Tioconazole or one of the above mentioned compounds can, of course, be administered alone. However, in keeping with standard pharmaceutical practice they are preferably administered in admixture with a pharmaceutical carrier to achieve more uniform distribution of the drug and to permit use of minimum drug concentrations sufficient to accomplish the intended purpose.

A favored topical vaginal dosage form is a cream as described above comprising from 1% to 2% by weight of one of said drugs. In each instance from about 1 to about 5 ml of said dosage form is applied intravaginally, desirably high in the vaginal vault. Greater amounts are generally avoided to minimize leakage.

The particular form of tioconazole or related compound enumerated above when used for control of herpetic infections in animals and humans is applied intravaginally prior to coitus. Alternatively, or even concurrently, it can be applied to consorts. For the chemotherapy of herpetic infections said drugs are administered topically to the site of infection and desirably to the immediate area surrounding said infection.

Their activity against HSV1 and 2 is determined by exposing a suspension of the virus at approximately $10^6$ pfu/ml in buffer or buffer plus 5% serum to the drug, e.g., tioconazole, for various periods of time. Aliquots are removed at the end of each time period and titrated immediately on Vero cell tissue culture monolayers. Plaques are counted after 2–3 days incubation at 37° C.

The in vitro evaluation of the anti-herpetic activity of the compounds is performed by determining the minimum inhibitory concentration (m.i.c.) of the test compounds in a suitable medium at which growth of the particular micro-organism fails to occur. In practice a series of agar plates, each having the test compound incorporated at a particular concentration are inoculated with a standard culture of HSV1 or 2 and each plate is then incubated for 24 hours at 37° C. The plates are then examined for the presence or absence of growth of the virus and the appropriate m.i.c. value is noted.

In this manner, tioconazole has been found to be virucidal against HSV1 and HSV2 even after relatively short contact periods at levels of 50 mg/ml or higher. Against HSV1 tioconazole, at 100 mg/ml, exhibited >99.9% reduction in infectivity after 24 hours. Against HSV2, 50 mg/ml achieved 95% reduction in infectivity after 20 minutes, and >99.9% reduction at one hour and 24 hours after contact. A concentration of 50 mg of tioconazole /ml achieved 95% and >99.9% reduction in infectivity after 20 and 60 minutes contact, respectively. However, after 24 hours of exposure no reduction in infectivity was observed with tioconazole at 50 mg/ml.

Representative formulations of tioconazole useful in this invention are presented below. The remaining agents disclosed herein are formulated and used in the same manner.

| TIOCONAZOLE VAGINAL TABLETS, 100 mg | |
|---|---|
| INGREDIENT | MG/TABLET |
| Tioconazole | 100.00 |
| Lactose | 644.00 |
| Corn starch | 372.00 |
| Magnesium stearate | 10.80 |
| Sodium lauryl sulphate | 1.20 |
| | 1,128.00 |

| | Tioconazole Cream 1% and 2% | |
|---|---|---|
| | g/Kg | |
| Ingredient | 1.0% | 2.0% |
| Tioconazole | 10.00 | 20.00 |
| White Soft Paraffin | 20.00 | 20.00 |
| Liquid Paraffin | 25.00 | 25.00 |
| Stearyl Alcohol | 55.00 | 55.00 |
| Stearic Acid | 45.00 | 45.00 |
| Cetomacrogol 1000* | 10.00 | 10.00 |
| Benzyl Alcohol | 10.00 | 10.00 |
| Propylene Glycol | 100.00 | 100.00 |
| Purified Water | 725.00 | 715.00 |
| | 1000.00 | 1000.00 |

*Identified in the Merck Index, 10th Edition, entry no. 7449, published by Merck & Co., Inc. 1983, as a polyethylene glycol fatty alcohol ether of formula $CH_3(CH_2)_m(OCH_2CH_2)_nOH$ where m may be 15–17 and n may be 20–24.

| Tioconazole Ointment 6.50% | |
|---|---|
| Ingredient | g/Kg |
| Tioconazole | 65.0 |
| Veegum F | 53.9 |
| White Soft Paraffin | 881.1 |
| | 1000.0 |

| Tioconazole Vaginal Ovules, 100 mg | | |
|---|---|---|
| Component | Grade | Mg/Ovule |
| Tioconazole | (91050) | 100.00 |
| Glycine (milled) | USP | 1250.00 |
| Lecithin (soya) | (93-CI-080) | 20.00 |
| Hydrogenated Vegetable Fat | (93-CI-081) | 160.00 |
| Beeswax | BP | 40.00 |
| Polysorbate 80* | EP | 30.00 |
| Liquid Paraffin, Liquid | PPC (1963) | 653.00 |
| | | 2253.00 |

*Sorbitan: mono-9-octadecenoate poly (oxy-1,2-ethanediyl), available from Atlas Chemical Industries, Inc. of Wilmington, Delaware.

I claim:

1. A method for the treatment of herpetic infections in a human infected thereby which comprises topically applying to the site of said infection an anti-herpetic amount of drug selected from the group consisting of tioconazole, econazole, clotrimazole, ketoconazole, butaconazole or a pharmaceutically acceptable acid addition salt thereof.

2. A method according to claim 1 wherein the drug is applied in the form of a cream or ointment comprising from about 1% to about 10% of said drug.

3. A method according to claim 2 wherein the drug is administered intravaginally.

4. The method according to claim 3 wherein the drug is tioconazole.

5. The method according to claim 3 wherein the drug is econazole.

6. The method according to claim 3 wherein the drug is clotrimazole.

7. The method according to claim 3 wherein the drug is butaconazole.

* * * * *